United States Patent
Register et al.

(10) Patent No.: US 10,835,757 B2
(45) Date of Patent: Nov. 17, 2020

(54) IMPLANTABLE OPTICAL STIMULATION AND DETECTION LEADS FOR NERVOUS TISSUE

(71) Applicant: The Charles Stark Draper Laboratory, Inc., Cambridge, MA (US)

(72) Inventors: Joseph J. Register, St. Petersburg, FL (US); Carlos A. Segura, Ipswich, MA (US); Gregg E. Favalora, Bedford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 373 days.

(21) Appl. No.: 15/957,551

(22) Filed: Apr. 19, 2018

(65) Prior Publication Data

US 2018/0304095 A1  Oct. 25, 2018

Related U.S. Application Data

(60) Provisional application No. 62/487,762, filed on Apr. 20, 2017.

(51) Int. Cl.
*A61N 5/00* (2006.01)
*A61N 5/06* (2006.01)
*A61N 5/067* (2006.01)

(52) U.S. Cl.
CPC ......... *A61N 5/0622* (2013.01); *A61N 5/0601* (2013.01); *A61N 2005/067* (2013.01);
(Continued)

(58) Field of Classification Search
CPC combination set(s) only.
See application file for complete search history.

(56) References Cited

U.S. PATENT DOCUMENTS

| 7,043,129 B2 * | 5/2006 | Auner | G02B 6/102 385/129 |
| 8,165,682 B2 * | 4/2012 | Gopalsami | A61B 5/01 600/378 |

(Continued)

OTHER PUBLICATIONS

International Preliminary Report on Patentability, dated Oct. 31, 2019, from International Application No. PCT/US2018/028364, filed Apr. 19, 2018. 10 pages.

(Continued)

*Primary Examiner* — Michael W Kahelin
*Assistant Examiner* — Shirley X Jian
(74) *Attorney, Agent, or Firm* — HoustonHogle LLP

(57) ABSTRACT

An optical neurostimulation and detection system and method are disclosed. The system includes a medical device including an implantable body, and a stimulation controller that connects to the medical lead device and provides a light source. One or more light emitter modules of the lead body couple light signals of the light source into modulated light signals, and the modulated light signals are emitted through the one or more light emitter modules to stimulate neural cells and/or neural tissue of a subject. In a preferred embodiment, the light emitter modules include a surface acoustic wave (SAW) transducer that couples the light source into the modulated light signals. Such a system provides emitted light incident upon the neural tissue of a much higher resolution than current systems and methods and can provide long-term implantation with fewer side effects and less tissue damage than current systems and methods.

21 Claims, 10 Drawing Sheets

(52) U.S. Cl.
CPC ............ *A61N 2005/0612* (2013.01); *A61N 2005/0653* (2013.01); *A61N 2005/0667* (2013.01)

(56) References Cited

U.S. PATENT DOCUMENTS

| | | | | |
|---|---|---|---|---|
| 8,165,692 | B2* | 4/2012 | Strother | A61N 1/37276 607/60 |
| 9,415,154 | B2 | 8/2016 | Leven | |
| 10,631,912 | B2* | 4/2020 | McFarlin | A61B 5/4893 |
| 2005/0215764 | A1* | 9/2005 | Tuszynski | C07K 14/435 530/358 |
| 2007/0100389 | A1* | 5/2007 | Jaax | A61N 1/36082 607/42 |
| 2007/0149952 | A1* | 6/2007 | Bland | G16H 50/20 604/890.1 |
| 2007/0287931 | A1* | 12/2007 | Dilorenzo | A61B 5/4839 600/545 |
| 2011/0125078 | A1* | 5/2011 | Denison | A61N 5/0601 604/20 |
| 2011/0172725 | A1* | 7/2011 | Wells | A61N 5/0622 607/3 |
| 2011/0295345 | A1* | 12/2011 | Wells | A61N 5/0603 607/89 |
| 2014/0039312 | A1* | 2/2014 | Rockweiller | A61B 5/1107 600/437 |
| 2014/0300695 | A1 | 10/2014 | Smalley et al. | |
| 2018/0085593 | A1* | 3/2018 | Fayram | H02J 50/80 |

OTHER PUBLICATIONS

Badreddine, A.H., et al., "Real-Time Imaging of Action Potentials in Nerves Using Changes in Birefringence," Biomedical Optics Express, 7(5): 1966-1973 (2016).

Boyden, E.S., "A History of Optogenetics: the Development of Tools for Controlling Brain Circuits with Light," F1000 Biology Reports, 3 (11): 1-12 (2011).

Geng, J., "Three-Dimensional Display Technologies," Advances in Optics and Photonics, 5: 456-535 (2013).

Go, M.A., et al. "Light-Neuron Interactions: Key to Understanding the Brain," J. Opt., 023002: 1-11 (2017).

Halle, M., "Autostereoscopic displays and computer graphics," Computer Graphics ACM SIGGRAPH, 31(2): 58-62 (1997).

Lutz, C., et al. "Holographic Photolysis of Caged Neurotransmitters," Nat. Methods, 5(9): 821-827 (2008).

Matteo, A. M., et al., "Collinear Guided Wave to Leaky Wave Acoustooptic Interactions in Proton-Exchanged $LiNbO_3$ Waveguides," IEEE Trans. on Ultrasonics, Ferroelectrics, and Frequency Control, 47 (1), 16-28 (2000).

Nikolenko, V., et al., "SLM microscopy: scanless two-photon imaging and photostimulation with spatial light modulators," Front. Neural Circuits, 2 (5) 1-14 (2008).

Partial Search Report of the International Searching Authority, dated Jul. 20, 2018, from International Application No. PCT/US2018/028364, filed on Apr. 19, 2018. 11 pages.

Perron, A., et al., "Optogenetics: Tools for Controlling and Monitoring Neuronal Activity," Progress in Brain Research (2012).

Qaderi, K., et al., Paired Leaky-Mode Spatial Light Modulators with 28° Total Deflection Angle, Optical Society of America, 1-5 (2017).

Schedl, D.C., et al. "Volumetric Light-Field Excitation," Scientific Reports, 6: 29193: 1-9 (2015).

Schermer, M., "Ethical issues in deep brain stimulation.," Front. Integr. Neurosci., 5(17): 1-5 (2011).

Smalley, D.E., et al., "Anisotropic Leaky-Mode Modulator for Holographic Video Displays," Nature, 498: 313-318 (2013).

Smithwick, Q. Y. J., et al., "Progress in holographic video displays based on guided-wave acousto-optic devices," Proc. SPIE 69L2, Practical Holography XXII: Materials and Applications, 69120H (2008).

Thompson, A.C., et al., "Optical Stimulation of Neurons," Current Molecular Imaging, 3(2): 162-177 (2014).

International Search Reprot and Written Opinion of the International Searching Authority, dated Sep. 12, 2018, from International Application No. PCT/US2018/028364, filed Apr. 19, 2018. 17 pages.

* cited by examiner

IMPLANTABLE OPTICAL STIMULATION AND DETECTION LEADS FOR NERVOUS TISSUE

RELATED APPLICATIONS

This application claims the benefit under 35 USC 119(e) of U.S. Provisional Application No. 62/487,762, filed on Apr. 20, 2017, which is incorporated herein by reference in its entirety.

BACKGROUND OF THE INVENTION

Stimulation of neural cells and/or neural tissue within a living subject, human or non-human, has traditionally been performed electrically through the use of medical lead devices that include electrodes. The electrodes are implanted into neural tissue of the subject such as the brain, spinal cord, and peripheral nerve fibers and nerve bundles. In one application, arrays of electrodes are implanted into brain tissue for Deep Brain Stimulation (DBS) of a subject for treating medical conditions such as Parkinsonian tremor. However, the electrodes can stimulate area beyond the targeted tissue, which causes common side effects such as mood and sensory changes, can cause implant injury, and cannot be implanted for an indefinite time period.

More recently, techniques that provide optical stimulation of neural cells and neural tissue have been proposed. These techniques replace the implanted metal electrodes of the traditional electrically-based neural stimulation methods with glass-based optical fiber. This reduces risk of injury and provides a large step towards long-term use of implanted neurostimulation systems for chronic illness. Typically, there are two types of optical neurostimulation techniques: optogenetic stimulation of genetically transfected cells using visible light, and direct application of pulsed infrared (IR) light to stimulate neurons without genetic transfection.

Optogenetics manipulates nerve cells genetically to create photo-sensitive ion channels in a neuron's cell membrane. In response to different wavelengths or pulses of visible light, the modified cells can either generate evoked action potentials (EAPs) or be electrically silenced. Genetic transfection of the neurons is commonly performed through electroporation or viral transfection methods. Opsins such as Channelrhodopsin-2 (ChR2) and Halorhodopsin (NpHR), in examples, modify the neural tissue genetically and enable excitation of the neural tissue in response to visible light. Channelrhodopsin-2 responds to blue light (473 nanometer (nm) wavelength) by creating evoked action potentials (EAP), where Halorhodopsin responds to yellow light (550 nm) by repolarizing the neuronal membrane to essentially cause the nerve to silence. Opsins now come in a wide-range of varieties, resulting in an array of wavelengths and switching times. See Boyden, E., "A history of optogenetics: the development of tools for controlling brain circuits with light," F1000 Biology Reports 3 (2011), doi:10.3410/b3-11.

Direct application of focused IR light upon nerve cells without the use of optogenetic transfection is another type of emerging neurostimulation technique. However, infrared neural stimulation that does not rely on the introduction of exogenous light responsive materials remains imperfectly understood, and techniques for accurately delivering light are still under development. See A. C. Thompson et al., "Optimal Stimulation of Neurons," Curr. Mol. Imaging 2014 July; 3 (2): 162-177. In this technique, fast pulses of IR light (typically on the order of milliseconds) are applied directly to the nerve cells, and EAPs can possibly be generated in nerve cells and/or the nerve cells can be silenced in response. However, the pulsed IR light currently lacks precision and may cause damage in non-targeted tissue regions. See Daria, V. R., "Light-neuron Interactions: Key to Understanding the Brain," Optics in the Life Sciences (2015), doi:10.1364/boda.2015.brt4b.3.

Other approaches involve optical stimulation of nerves through optical fiber and waveguide emitters but tend to provide less resolution in the modulated light signals that are created. For example, a system described in U.S. Pat. App. Pub. No. US2010/0172725A1, entitled "Nerve Stimulator and Method Using Simultaneous Electrical and Optical Signals" to Wells et al. ("Wells") discloses in vivo neural stimulation using implantable optical emitters including waveguides.

Also, some research has been done with Digital Micromirror Devices (DMD) and other pixel-based spatial light modulators. However, these can be bulky systems with large optical paths and therefore are not suitable for implantation. See also: C. Lutz, T. S. Otis, V. DeSars, S. Charpak, D. A. DiGregorio, and V. Emiliani, "Holographic photolysis of caged neurotransmitters," Nat. Methods, 5 (9), 821-7, (September 2008); V. Nikolenko, B. O. Watson, R. Araya, A. Woodruff, D. S. Peterka, and R. Yuste, "SLM microscopy: scanless two-photon imaging and photostimulation with spatial light modulators," Front. Neural Circuits, 2:5 (19 Dec. 2008); D. C. Schedl and O. Bimber, "Volumetric Light-Field Excitation," Scientific Reports, 6, 29193 (2016).

SUMMARY OF THE INVENTION

Three-dimensional (3D) display technologies utilize various light field generators to produce high-resolution light fields. The light field generators project spots of light in space at different angles, intensities, and colors and have typically been utilized in the fields of holography and virtual reality, such as for creation of holographic images and autostereoscopic displays. Recently, researchers have begun applying the light fields generated by the 3D display technologies to the medical field for optical stimulation of neural tissue and cells.

The present invention concerns an optical neurostimulation system that includes a medical device having an implantable/in vivo lead body. The implantable lead body utilizes and incorporates one or more light field generators possibly similar to and leveraged from 3D display technologies. The medical device enables 3D stimulation and "addressing" of points of light within and/or upon a neural tissue volume of a subject, such as individual nerve fibers and nerve bundles, in examples. The lead body receives light signals from a light source or generates the light, and light emitter modules of the lead body generate modulated light signals from the light signals. The modulated light signals are then emitted from the modules onto the target neural tissue, and stimulate the neural tissue by generating EAPs, for example, in the neural tissue and/or by electrically silencing the neural tissue. The level of image sharpness and resolution provided by such a device is much greater than that provided by existing optical neurostimulation techniques and systems.

The proposed optical neurostimulation system is different from some existing medical lead devices due to the use of diffractive and non-diffractive optical elements within the medical lead device. In a preferred embodiment, an implantable lead body of the medical lead device uses surface acoustic travelling waves (SAW) as diffractive elements to provide greater flexibility over existing pixel-based modulators.

In one embodiment, the medical lead device utilizes a 3D display technology known as "spatially multiplexed display" to create the modulated light signals for stimulating nerve cells/nerve tissue of a subject. In one implementation, the spatially multiplexed display can use an array of organic light emitting diodes (OLED) as a light source, which creates optical signals in the form of an array of pixels. The array of pixels are then mapped to regions of space by an interposed array of lenslets, where each lens of the lenslets covers a group of pixels. Other implementations, such as multiplexed displays based on LEDs and Vertical Cavity Surface Emitting Lasers (VCSELs), are alternatively or additionally employed, in examples.

In the preferred embodiment, the medical lead device utilizes a light field generating technology known as "leaky-mode" surface acoustic wave (SAW) coupling. For this purpose, the lead body integrates an acousto-optic device such as a leaky mode SAW transducer within each of the light emitter modules, where the SAW light emitter modules couple the optical signals of a light source into a high-resolution modulated light signal.

In embodiments, the inventive optical neurostimulation system also has other advantages over existing neurostimulation systems and methods. In one example, the implantable medical lead device can be made functionally in a more compact form factor. This allows for scaling the device down to the size-scale of nerves and/or nerve bundles. The compact form factor enables implantation into tight spaces in the body for intrafascicular nerve stimulation and intracranial applications. In other examples, such a system also provides a wider steerable angle than existing systems, does not lock the illumination volume into discretized shapes, and also provides better spatial resolution through the use of truly diffractive optical elements (such as through the use of SAW signals).

Embodiments also incorporate a linked chain of spatial light modulators. While it may be possible to create a linked chain of pixel based modulators (SLMs) the interconnects involved (thousands to millions of wires) would prevent the device from being useful in vivo due to its heft. The analog nature of SAW devices, on the other hand, allows for the addressing of extremely high densities of spatially resolved points within the tissue volume with minimal radio frequency (RF) or optical drive lines.

It is also important to note that the present invention can be applied to treat a wide variety of neurological conditions beyond that of Parkinson's Disease and other movement-related disorders. In examples, the invention can be utilized to treat conditions that involve peripheral nerves such as bladder dysfunction, sexual dysfunction, or even the restoration of touch to patients with lost limbs.

In general, according to one aspect, the invention features an optical neurostimulation system. It comprises a medical lead device including an implantable lead body and one or more light emitter modules of the lead body that generate modulated light signals for the irradiation of neural tissue of a subject.

In embodiments, the one or more light emitter modules are attached to a substrate of the lead body, and might be molded into a substrate of the lead body.

A nerve cuff can be used for attaching the light emitter modules onto the neural tissue of the subject.

One or more optical drive lines might be provided that connect to and enable the one or more light emitter modules to receive the light signals. In a preferred embodiment, the one or more optical emitter modules include Surface Acoustic Wave (SAW) substrates in which SAWs are generated to couple the modulated light signals into the neural tissue. In such case, the lead body might include one or more radio frequency (RF) drive lines that connect to and enable the one or more light emitter modules to receive RF signals which control the generation of the SAWs.

In some illustrated embodiments, the modulated light signals are emitted from a distal face of the one or more light emitter modules. In other embodiments, however, these modulated light signals might be emitted from the proximal faces or the end faces of those modules.

In some embodiments, a stimulation controller includes the light source and controls the coupling of the light signals into the modulated light signals provided by the one or more light emitter modules. This stimulation controller could even be implantable.

In some embodiments, the light emitter modules are arranged around the lead body in a circumferential fashion. In some cases, those modules may comprise two dimensional arrays of display elements such as organic light emitting diodes. Light directing elements could further be arranged over the display elements.

In general, according to another aspect, the invention features a medical lead device. This device comprises an implantable lead body, a flexible umbilical tether including optical drive lines that provide light signals to the lead body, and one or more light emitter modules of the lead body that couple the light signals into modulated light signals that are emitted through the one or more light emitter modules to stimulate neural cells and/or neural tissue of a subject.

In general, according to still another embodiment, the invention features a medical lead device. As before, it comprises an implantable lead body and a flexible umbilical tether including optical drive lines that provide light signals to the lead body. This embodiment, however, has provisions for detecting optical signals from the tissue. Specifically it has one or more light emitter and detector modules that provide light to stimulate neural cells and/or neural tissue of a subject and collected from the tissue or cells.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 5A-5D show views of and details of operation for different exemplary spatially multiplexed displays, where the spatially multiplexed displays can also be integrated within a light emitter module for coupling light signals from a light source into modulated light signals for optical stimulation of neural tissue, in which FIG. 5A is a schematic perspective view of a flexible display, FIG. 5B is a schematic top view of the flexible display of FIG. 5A, FIG. 5C is a schematic side view showing the operation of a subpixel of the flexible display of FIG. 5A, and FIG. 5D;

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
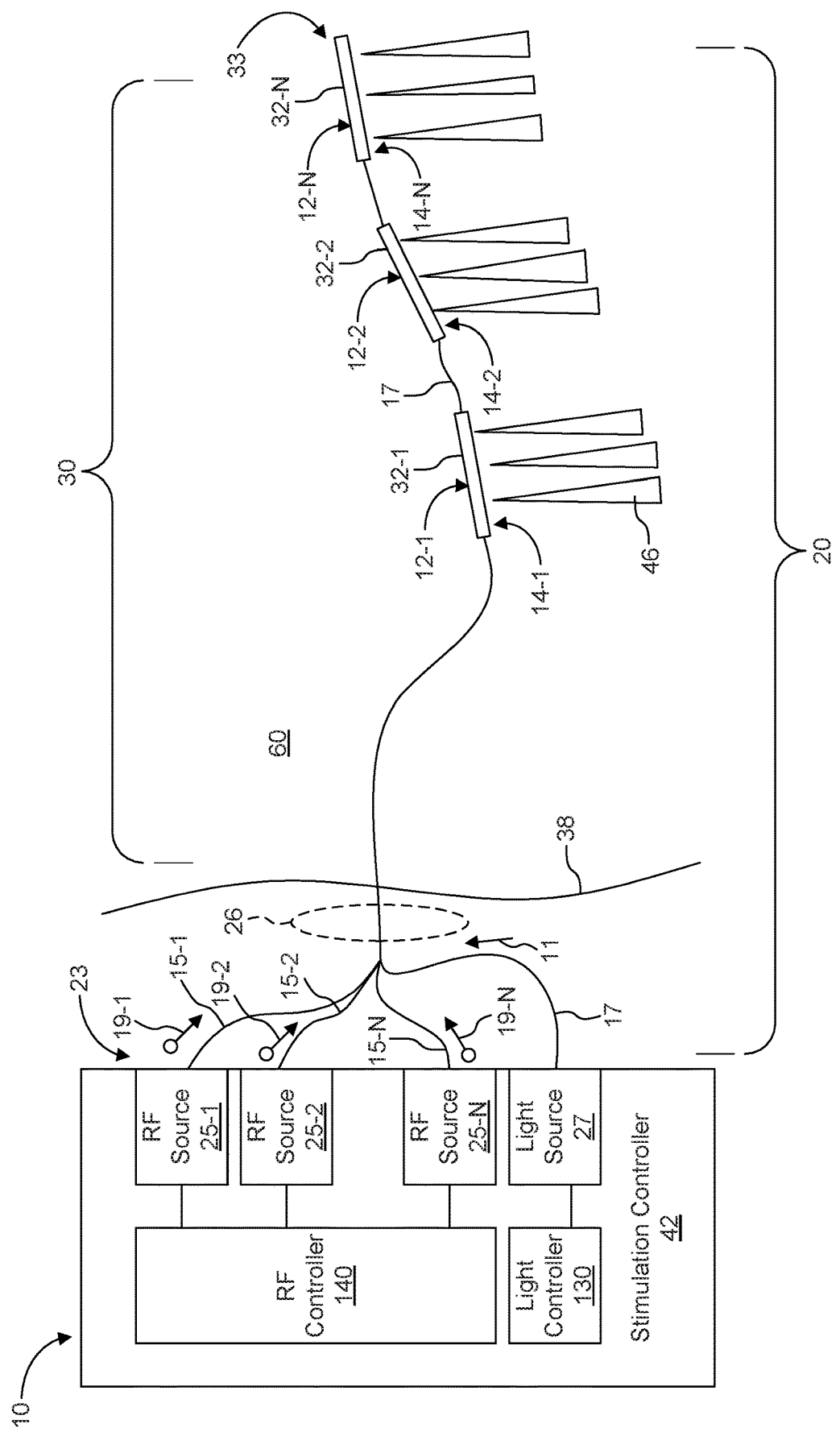
FIG. 1 is a schematic diagram of an optical neurostimulation system that includes an implantable lead body of a medical lead device and a stimulation controller, where the lead body includes light emitter modules that couple light signals from a light source into modulated light signals that are emitted from the light emitter modules to stimulate neural tissue such as neural cells of a subject.

FIG. 1 is a schematic diagram of an exemplary optical neurostimulation system 10, which has been constructed according to the principles of the present invention.

The system 10 includes a stimulation controller 42 and a medical lead device 20. The medical lead device 20 has an elongated lead body 30 and a flexible umbilical tether 26. A distal end 33 of the medical lead device 20 includes one or more light emitter modules 32 of the lead body 30 and a proximal end 23 of the medical lead device 20 includes radio frequency (RF) and optical terminations of the flexible umbilical tether 26.

The RF and optical terminations of the flexible umbilical tether 26 connect the medical lead device 20 to the stimulation controller 42. The flexible umbilical tether 26 is located outside and crosses the body/skin boundary 38 of the subject 60 as shown, but can also be implanted in the subject 60. The flexible umbilical tether 26 includes one or more RF drive lines 15 and includes one or more optical drive lines 17, in the illustrated example.

The lead body 30 is implanted within a subject 60 for the purpose of photostimulation of nervous tissue 99 including nerves of the subject 60.

The stimulation controller 42 includes an RF controller 140, a light controller 130, one or more RF sources 25, and one or more light sources 27. The RF controller 140 controls the RF sources 25 and the light controller 130 controls the light sources 27. The stimulation controller 42 is either percutaneous or implantable (i.e. inserted behind the skin boundary 38) and includes the necessary subsystems for generation of light signals 11 and RF signals 19 required by the light emitter modules 32.

In the illustrated embodiment, the light source 27 provides light signals 11 via an optical drive line 17 to the light emitter modules 32 of the lead body 30. In one example, the light source might be an individual laser or an array of lasers, or even different lasers emitting at different wavelengths.

On the other hand, in the illustrated embodiment, separate RF sources 25-1, 25-2, and 25-N send RF signals 19-1, 19-2, and 19-N via separate RF control lines 15-1, 15-2, and 15-N for individual controlling modulation delivered to each of the light emitter modules 32-1, 32-2, and 32-N, respectively.

In examples, the optical drive line 17 can be a single mode or multimode optical fiber, the former having a much smaller carrying core than the latter and is therefore suitable for smaller applications and minimizing the trauma to body in which the system is installed.

In the illustrated embodiment, though only one light source 27 providing a common light signal 11 via a single optical drive line 17 to all light emitter modules 32 is shown, the stimulation controller 42 in conjunction with the flexible umbilical cord 26 can also provide separate light signals 11 to each of the light emitter modules 32 via separate optical drive lines 17 for each of the light emitter modules 32.

Each of the light emitter modules 32-1, 32-2, and 32-N has a proximal face 12-1, 12-2, and 12-N and a distal face 14-1, 14-2, and 14-N. In the illustrated configuration, the distal face is the exit face, i.e., the face through which the light signals 46 are delivered to tissue of the subject 60. Preferably, the light emitter modules 32 emit modulated light signals 46 via the exit faces 14 of the modules 32.

Figure 2:
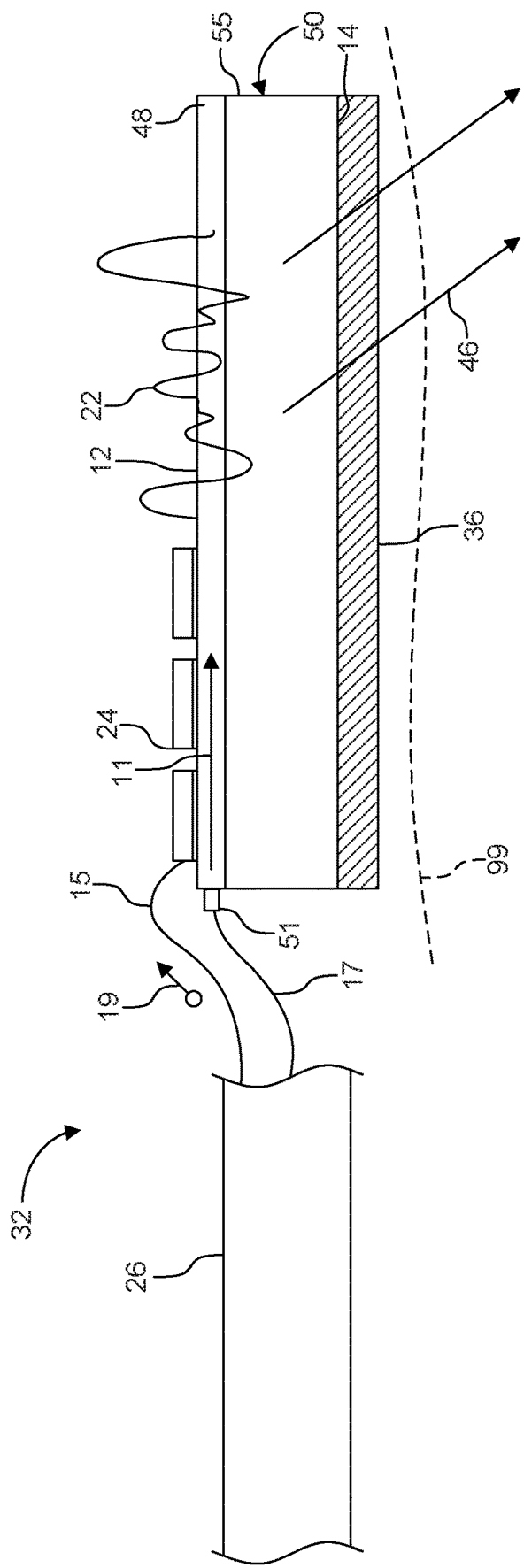
FIG. 2 is a schematic diagram showing a preferred embodiment of an exemplary light emitter module of the lead body of the medical lead device in FIG. 1, where the light emitter module is a SAW light emitter module that generates SAW signals, which in turn couple the light signals into the modulated light signals.

FIG. 2 shows detail for a SAW optical modulator embodiment of the light emitter modules 32, also referred to as a SAW light emitter module 32. The SAW light emitter module 32 has a SAW substrate 50 that is typically adjoined to or molded into a flexible substrate 36 of the lead body 30.

For details of operation and fabrication of SAW transducer devices and leaky-mode acousto-optic devices in general, see D. E. Smalley et al, "Anisotropic leaky-mode modulator for holographic video displays," Nature, doi: 10.1038/nature12217 (2013); U.S. Pat. App. Publ. No. US201410300695A1, published Oct. 9, 2014, entitled "Full-parallax Acousto-Optic/Electro-Optic Holographic Video Display" to D. E. Smalley et al; Anna Maria Matteo, Chen S. Tsai, and Nhan Do, "Collinear Guided Wave to Leaky Wave Acoustooptic Interactions in Proton-Exchanged LiNbO3 Waveguides," IEEE Trans. on Ultrasonics, Ferroelectrics, and Frequency Control, 47 (1), t6-28 (January 2000); and D. E. Smalley, Q. Y. J. Smithwick, V. M. Bove Jr., J. Barabas, and S. Jolly, "Anisotropic leaky-mode modulator for holographic video displays," Nature, 498, 313-317 (20 Jun. 2013).

In one example, the SAW substrate 50 of the SAW light emitter module 32 is molded into the flexible substrate 36 by etching the flexible substrate 36. It can also be bonded to the substrate 36. The flexible substrate 36 is typically fabricated from a biocompatible material that is mechanically compliant and can chemically support the steps of microfabrication. Suitable materials include polyimide, parylene, and various fluoropolymers, in examples. The flexible substrate 36 can also include RF and optical interconnects that connect the RF drive lines 15 carrying the RF signals 19 and the optical drive lines 17 carrying the optical signals 11 to each of the SAW light emitter modules 32, in some embodiments.

In the illustrated example, the lead body 30 is fabricated such that the exit faces 14 of the SAW light emitter modules 32 are presented in a segmented row along/upon the flexible substrate 36. The distance between each adjoining module typically ranges from 500 micrometers (um) for smaller applications such as imaging of single nerve fibers in the PNS of a subject 60 to as much as 1 centimeter (cm) for deep-brain applications. Each module 32 also has a thin form factor so that it is collinear with the overall form of the lead body 30. The width of each module 32 is typically on the order of 500 micrometers to 3 millimeters (mm) and it has similar dimensions in depth. The length of each module 32 typically ranges from 1 mm to 20 mm. Collectively, the modules 32 are adjoined to (or molded into) the flexible backplane interconnecting substrate 36.

The SAW light emitter module 32 uses the principles associated with operation of leaky-mode surface acoustic wave (SAW) transducer devices to couple the guided mode light signals 11 into modulated light signals 46. For this purpose, each SAW light emitter module 32 includes a transducer 24, e.g., an interdigitated transducer (IDT), which is typically patterned upon the SAW substrate 50 and a waveguide 48 that is typically fabricated in the SAW substrate 50. Typically, the waveguide 48 is anisotropic and only guides light in one polarization.

An in-coupling device 51 is used to couple the input light carried in an optical fiber 17, for example, into the waveguide 48. Examples of in-coupling devices 51 include in-coupling prisms, gratings, or simply butt-coupling between the optical fiber 17 and the waveguide 48. The input light is launched into a guided mode upon entry into the waveguide 48. Commonly, the TE (transverse electric) mode is guided.

The waveguide 48, e.g., slab waveguide, is typically created in a lithium niobate substrate 50 by proton-exchange. The transducer 24 induces the SAWs 22 in the substrate 50 that propagate along the waveguide 48. Such transducers 24 are often driven electrically, e.g. using a 300-500 MHz radio frequency (RE) drive signal 19.

The guided light 11 interacts with the SAW 22. The result of this interaction between the SAW 22 and the light in the waveguide 48 is that a portion of the guided light is polarization-rotated, out of the guided mode and into a leaky mode having the transverse magnetic (TM) polarization. The light then exits the waveguide 48 as leaky-mode or diffracted light 46 propagates through the substrate 50. At some point this diffracted light 46 exits the substrate 50. In different examples, the light may also exit out distal face 14, end face 55 or proximal face 12 as exit light.

In the illustrated example, the emitted modulated light signals 46 propagate through the flexible substrate 36, and are then incident upon the neural tissue 99 of the subject 60, where the neural tissue 99 is adjacent to the exit face 14 of each SAW light emitter module 32. Based upon the optical stimulation properties of the emitted modulated light signals 46 incident upon the neural tissue 99, the emitted modulated light signals 46 create evoked action potentials (EAPs) in the nerve tissue 99 and/or silence the action potentials of the nerve tissue 99.

The pattern of the modulated light signals 46 of each SAW light emitter module 32 is along the length of each waveguide 48 and is controlled by the RE signals 19. The R' signals 19 can be modulated in intensity and/or frequency for this purpose via the RF controller 140 of the stimulation controller 42.

Figure 3:
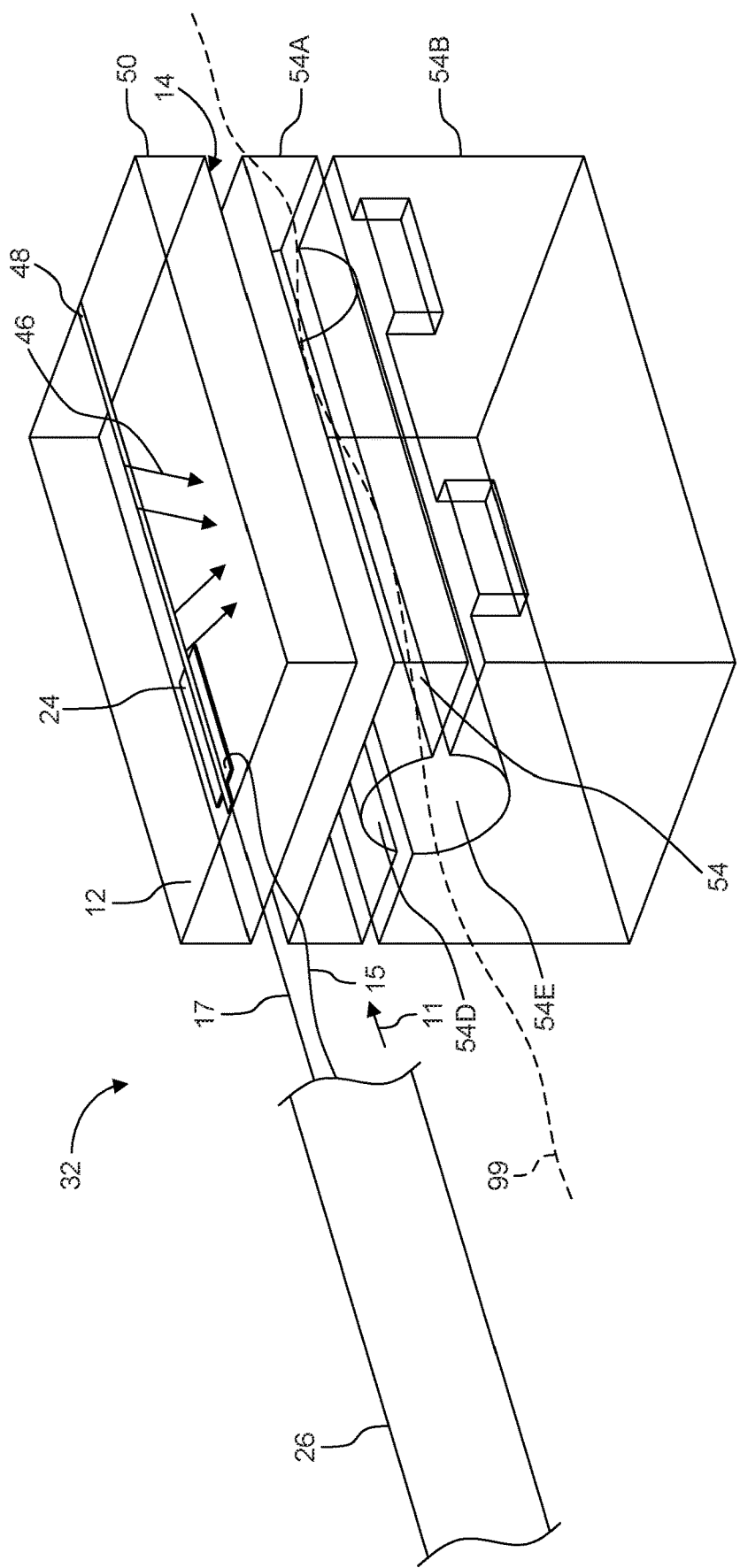
FIG. 3 is a perspective partially exploded view of another embodiment of a light field generator, e.g., SAW light emitter module, where an optogenetic nerve retainer cuff is attached to the generator for stimulation of nerve tissue in a peripheral nervous system (PNS) of the subject.

FIG. 3 shows an embodiment of a SAW light emitter module 32 fastened to an optogenetic nerve retainer cuff 54 for PNS applications. The high spatial resolution provided by the SAW light emitter module 32 can more accurately replicate sensory signal stimulation over the surface of the nerve or nerve cord/bundle 99 than traditional electrical stimulation systems and methods. Though a SAW light emitter module 32 is shown, various other light field generators can alternatively be incorporated into the light emitter module 32, such as a spatially-multiplexed display, in one example.

Existing approaches to stimulation of nervous tissue 99 using nerve cuffs have limitations. For example, some existing neurostimulation devices have attempted to provide multichannel optical stimulation, but the waveguide density (volumetric/packing factor) limitations often limit the resulting stimulation resolution of these attempts. See U.S. Pat. App. No. 2011/0295345A1, entitled "Implantable infrared nerve stimulation devices for peripheral and cranial nerve interfaces," to Wells et al. With regard to electrical stimulation approaches, in another example, these approaches typically utilize Utah arrays of multiple electrodes that stab the nerve 99 to gain local spatial precision. The resulting glial activation and scarring causes the eventual interface degradation. See Branner, A., Stein, R, Fernandez, E., Aoyagi, Y., & Normann, R., "Long-Term Stimulation and Recording With a Penetrating Microelectrode Array in Cat Sciatic Nerve," IEEE Transactions on Biomedical Engineering, 51, (1), 46-157 and FIG. 6, doi:10.1109/tbme.2003.820321.

In contrast, the optical imaging technique provided by the nerve cuff 54 remains mostly non-invasive to the nerve 99 and the holographic nature of the stimulation provided by the modulated light signals emitted from the SAW modules 32 provides unprecedented spatial control of the optical stimulation within the neural tissue 99.

In more detail, the SAW substrate 50 is clamped to a target peripheral nerve 99 via the nerve retainer cuff 54 of each SAW light emitter module 32. In one example, the nerve cuff 54 is fabricated from a suitable biocompatible polymer though micro molding and affixed to the SAW optical emitter module 32. In the illustrated example, the nerve cuff comprises an upper half 54A and a lower half 54B that sandwich the nerve 99 between them. Specifically, the nerve 99 sits in a channel formed by a semicircular groove 54D formed in and running along the length of the upper half 54A and a second semicircular groove 54E formed in and running along the length of the lower half 54B of the nerve cuff 54. The nerve 99 is passed through this channel in the retainer cuff 54 and locked in place by bonding or clamping the upper half 54A to the lower half 54B of the nerve cuff 54. In turn, the distal face 14 of the SAW substrate 50 is then bonded to an upper face of the upper half 54A.

Preferably, multiple SAW light emitter modules 32 are deployed to cover the transverse and sagittal plane of the nerve 99. The conductors coming from the nerve cuff 54 can either be pre-fastened to the modules 32 or locked onto the modules 32 after the nerve 99 is secured. The modulated light signals 46 collectively emitted by the SAW light emitter modules 32 provide a controllable light field across the clamped peripheral nerve 99. Additionally and/or alternatively, the SAW light emitter modules 32 having the nerve retainer cuff 54 can be utilized in conjunction with optogenetic modification of the target neural tissue 99.

Figure 4A:
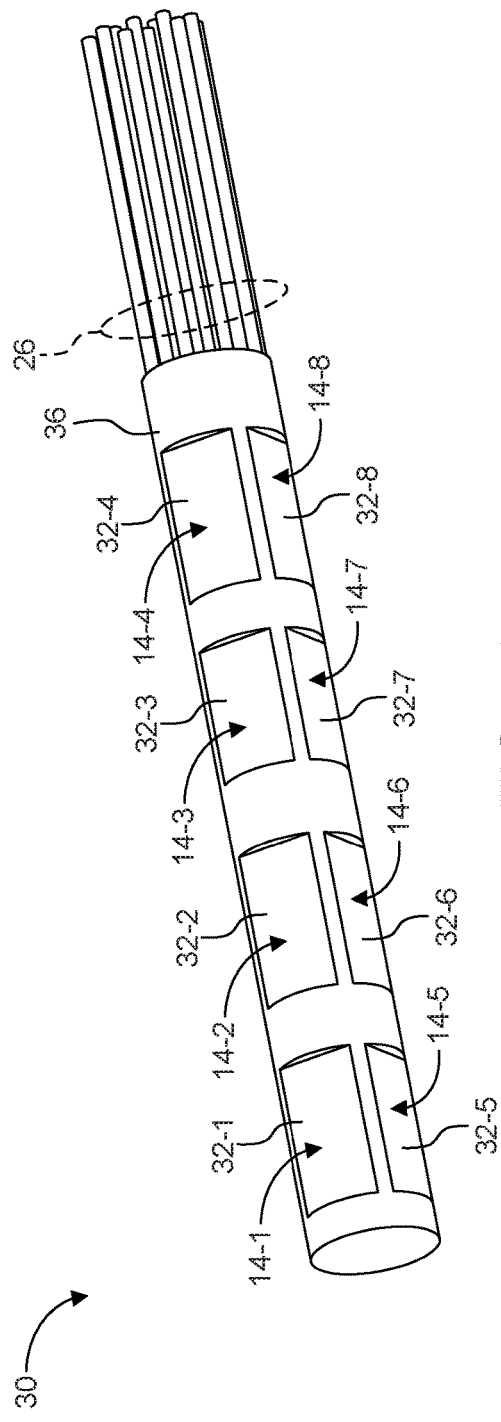
FIGS. 4A and 4B are a perspective view and another partial perspective view of an embodiment of the lead body of the medical lead device including multiple SAW light emitter modules arranged in a circumferential fashion about the lead body of the medical lead device.
Figure 4B:
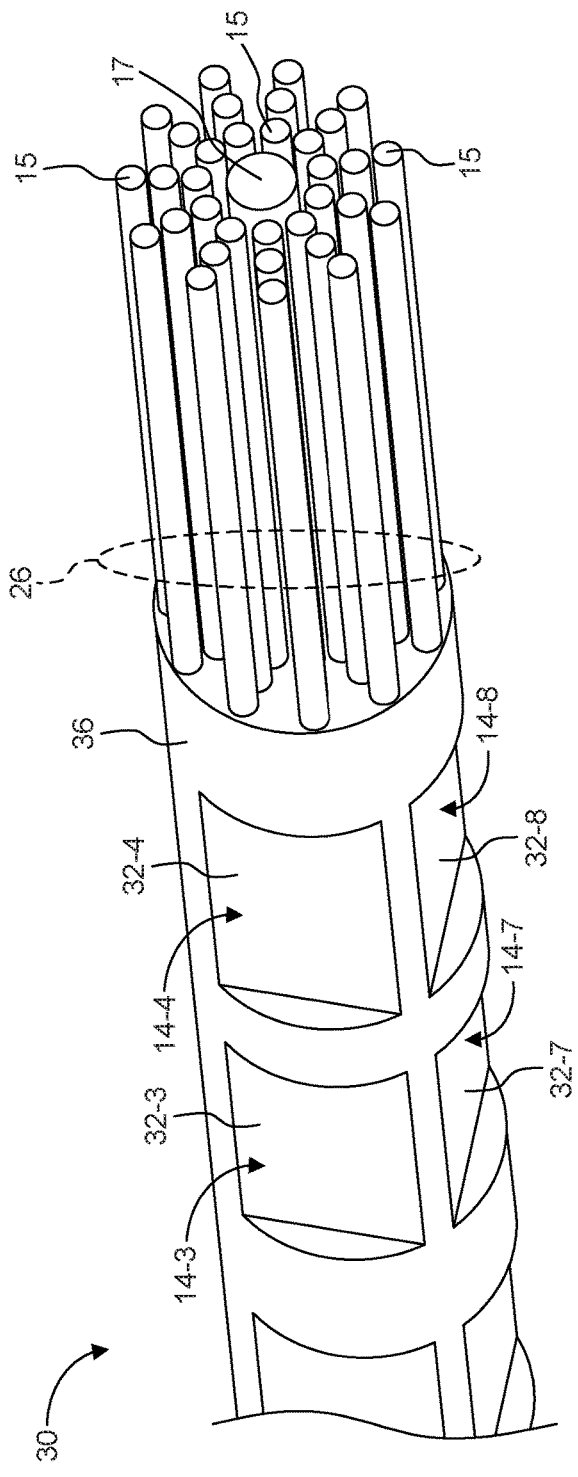

FIGS. 4A and 4B show an embodiment of the lead body 30 having multiple SAW light emitter modules 32-1 through 32-8 arranged in a circumferential fashion about the lead body 30 and set into a flexible substrate 36 of the lead body 30. Because the lead body 30 can be positioned within a tissue volume and can be moved, such as by rotating the lead body 30 about the axis of the lead body 30, this embodiment enables "steering" of the emitted modulated light signals 46 within/upon the entirety of the volume of neural tissue 99 surrounding the lead body 30. This can be achieved because the modulated light signals 46 typically exit only from the distal exit faces 14-1 through 14-8 of the separate SAW light emitter modules 32-1 through 32-8, respectively.

Such an arrangement of light emitter modules 32 especially aids in positioning of the lead body 30 for deep brain applications when the rotation of the lead body 30 about its primary axis is critical. Although not illustrated, it can be understood that this configuration projects an approximately radial pattern or volume of emitted modulated light signals 46 that typically resembles a radiation pattern of a dipole antenna, with the lead body 30 situated coaxially within the pattern.

In the illustrated embodiment, a single optical drive line 17 supplies light to multiple SAW light emitter modules 32-1 through 32-8. Light can be coupled from the line 17 to the modules 32 using gratings. Separate RF signals are supplied to each of the SAW light emitter modules 32-1 through 32-8 via RF control lines 15 arrayed around the optical drive line. Preferably the substrate 36 of the lead body encapsulates the optical drive line(s) 17 and RF control lines 15 and the proximal faces of the SAW substrates SAW light emitter modules 32-1 through 32-8 to provide a compact yet tough lead body 30.

FIGS. 5A-5D show components of different spatially multiplexed displays that can also be built at a scale suitable for integration into the light emitter modules 32 for generating modulated light signals 46 for irradiation tissue such as neural tissue 99.

Figure 5A:
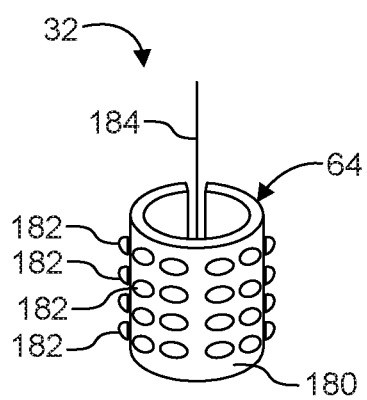

In FIG. 5A, an exemplary flexible spatially-resolved display 64 of a light emitter module 32 is fabricated using a sheet 180 of organic light emitting diodes (OLEDs). The sheet 180 of OLEDs are rolled into a tubular configuration. Power and data are received from the stimulation controller 42 via an axially-running cable 184. The two dimensional array of OLED display elements of the sheet 180 emit light that is collimated and directed by light-directing elements 182 arranged over the sheet 180. The light directing elements can be lenslets or directional gratings, in two examples. This provides functionality similar to an autostereoscopic display.

Figure 5B:
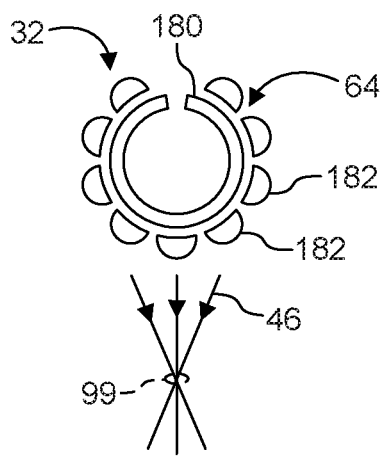

A top view of the OLED-based light emitter module 32 is shown in FIG. 5B. The modulated light signals 46 are generated by the OLEDs of the sheet 180 and formed by the light-directing elements 182 arranged over the OLEDs. In the illustrated example, the modulated light signals 46 originated from several OLEDs of the sheet 180 and guided by several light-directing elements 182 are thus directed to a signal activation site in the neural tissue 99.

Figure 5C:
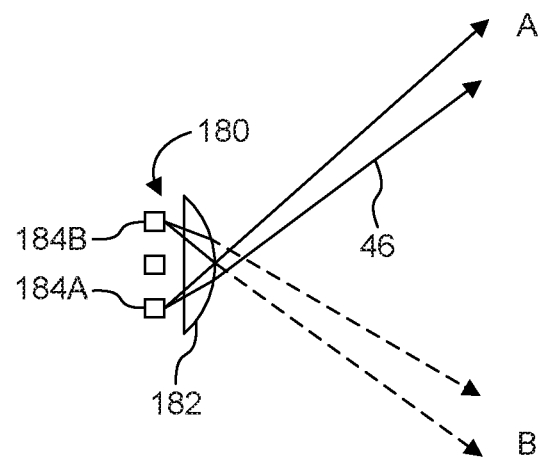

FIG. 5C provides detail for a mode of operation of the OLED-based spatially multiplexed display 64 in FIGS. 5A-5B. Here, several sub-pixel constituents of OLEDs 184A and 184B of the sheet of OLEDs 180 are selectively energized to generate modulated light signals 46 in direction A or direction B. The different beams are formed by a shared light-directing element 182 that is associated with and positioned over the OLEDs 184A and 184B.

Figure 5D:
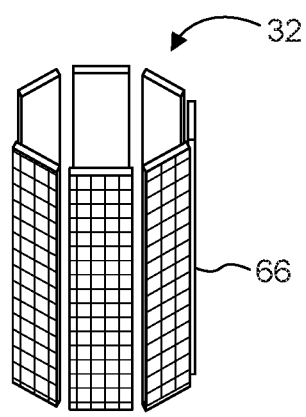

FIG. 5D shows another example of a spatially multiplexed display 64 that can be integrated within a light emitter module 32, an arrangement of integral photography panels 66. Each of the panels 66 are typically 2D projectors, and arranging the panels in a circular fashion enables the light to be projected in all directions. The integral photography panels 66 are also known as fly's-eye lens arrays and light fields displays. Yet another spatially multiplexed display 64 that can be integrated within and at the scale of the light emitter modules 32 is a lenticular array.

It can also be appreciated that modulating light field generators other than spatially multiplexed displays and SAW transducers can be integrated within and at the scale of the light emitter modules 32. In one example, a scanned illumination display such as a strobed/cascading light source behind a transmissive spatial light modulator (SLM) with a light-directing element following it (e.g. a long lens segment) can couple the light signals 11 into the modulated light signals 46. In another example, a pixelated hologram such as an amplitude or phase-modulated SLM configured to act as a hologram can couple the light signals 11 into the modulated light signals 46.

Figure 6:
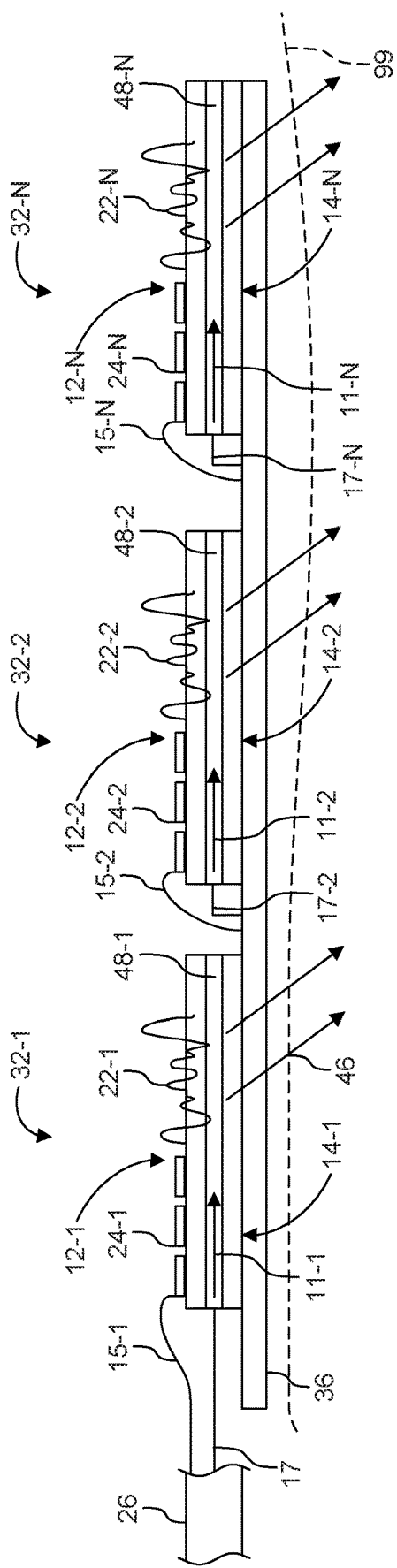
FIG. 6 is a schematic side view showing an embodiment of the lead body that includes exemplary SAW light emitter modules which are adjoined or molded into a flexible substrate of the lead body.

FIG. 6 shows multiple SAW light emitter modules 32-1, 32-2, and 32-N bonded or molded into the flexible substrate 36 of the lead body 30. Light signals 11-1, 11-2, and 11-N carried by optical drive lines 17-1, 17-2, and 17-N are diffracted from the waveguides 48 into modulated light signals 46. In this embodiment, there is a separate optical drive line 17 for each of the emitter modules 32. The modulated light signals 46 exit the light emitter modules 32-1, 32-2, and 32-N at distal or exit faces 14-1, 14-2, and 14-N. The modulated light signals 46 then propagate through the flexible substrate 36 and into the neural tissue 99.

The light signals 11-1, 11-2, and 11-N are diffracted into the modulated light signals 46 by the SAWs 22 generated by the DT's 24-1, 24-2, and 24-N of light emitter modules 32-1, 32-2, and 32-N receiving RF control signals 19-1, 19-2, and 19-N carried by RF drive lines 15-1, 15-2, and 15-N. The RF control signals 19-1, 19-2, and 19-N cause the IDTs 24-1, 24-2, and 24-N to generate the SAW signals 22-1, 22-2, and 22-N that are modulated in accordance with the amplitude and/or phase of the RE control signals 19. The SAW signals 22-1, 22-2, and 22-N then diffract the light signals 11-1, 11-2, and 11-N out of the waveguides 48-1, 48-2, and 48-N to produce the modulated light signals 46.

Figure 7:
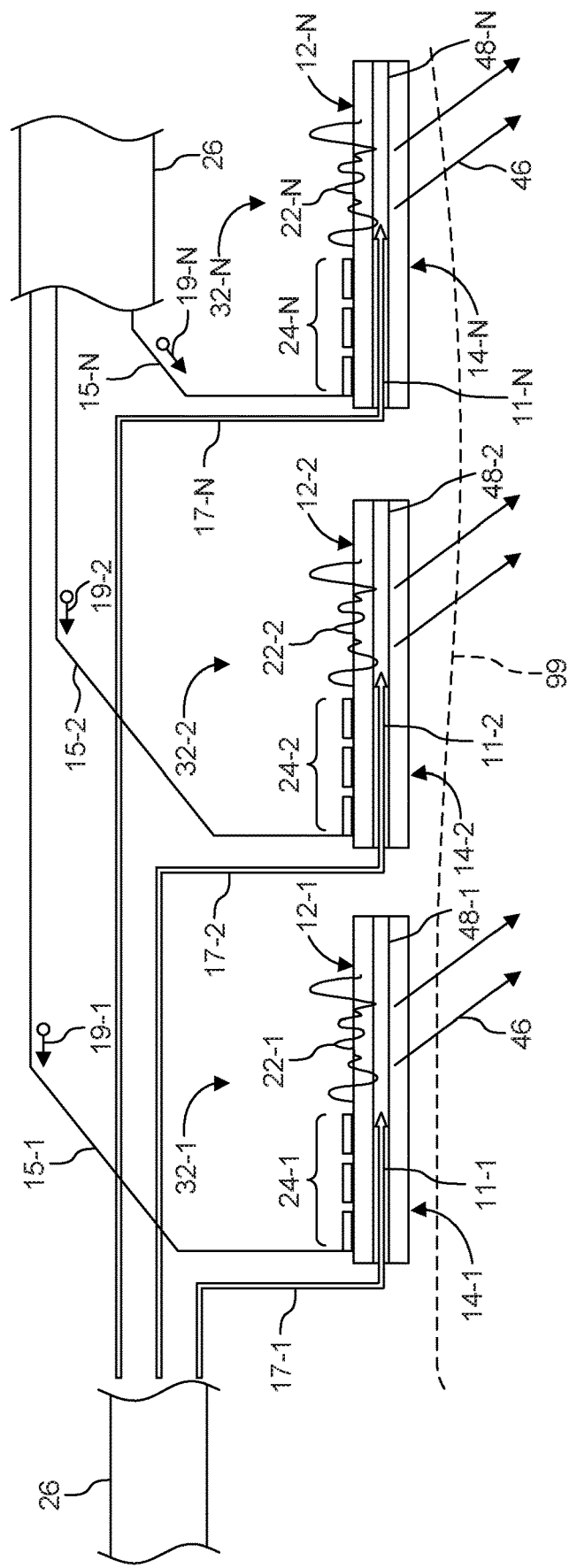
FIG. 7 is a schematic side view of the lead body showing more detail for individual optical drive lines and individual RF drive lines of a flexible umbilical tether of the medical lead device that connect the stimulation controller to each of the SAW light emitter modules of the lead body in FIG. 6.

FIG. 7 shows more detail for the connections between the optical drive lines 17 and RF drive lines 15 of the flexible umbilical cord 26 and the SAW light emitter modules 32 in FIG. 6. Separate optical drive lines 17-1, 17-2, and 17-N and RF drive lines 15-1, 15-2, and 15-N of the flexible umbilical cord 26 connect to each of the SAW light emitter modules 32-1, 32-2, and 32-N.

Figure 8:
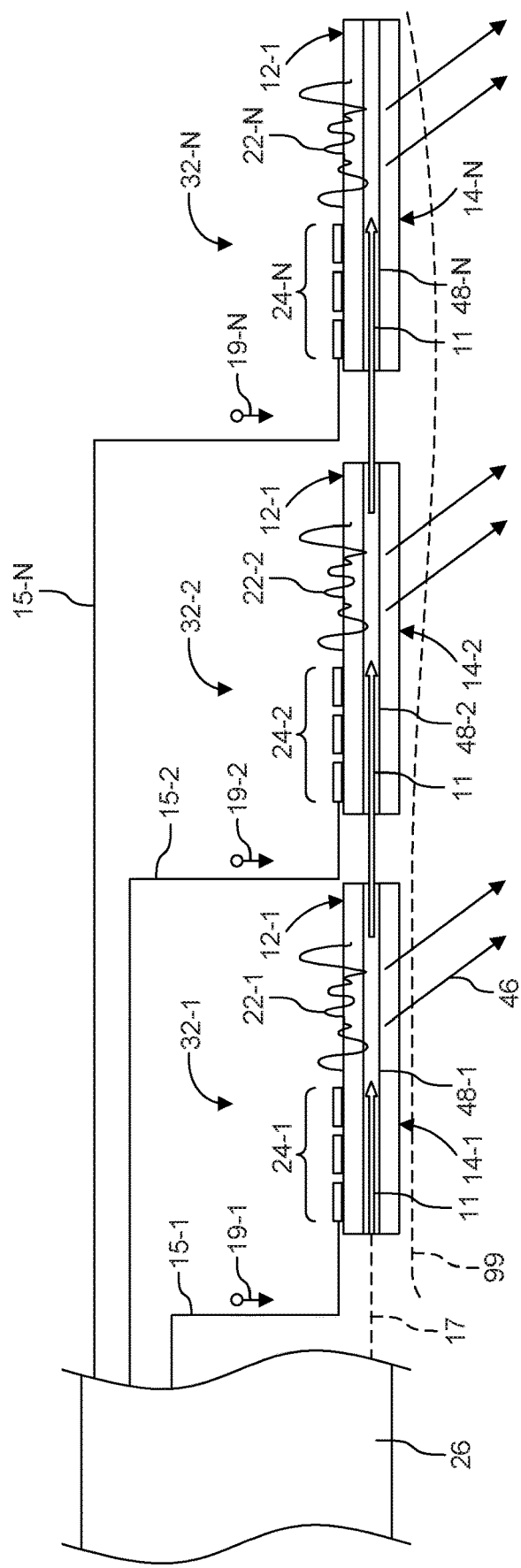
FIG. 8 is a schematic side view of the lead body showing detail for the drive lines of the flexible umbilical tether for the lead body of FIG. 6, where a single optical drive line provides a common light signal to each of the SAW light emitter modules.

FIG. 8 shows a different embodiment in which a single optical drive line 17 provides a common light input signal 11 for banks of SAW light emitter modules 32 arranged along a line in a daisy chained arrangement. By connecting the output of SAW module 32-1 to the input of the next SAW module 32-2 and then iteratively connecting the output of SAW 32-2 module to the input of SAW module 32-N, the optical interconnect scheme can be simplified to enable the lead body 30 and its modules 32 to be slimmer as compared to the lead body 30 of FIG. 7. The drawback of this technique is that each optical interconnect junction and each module 32 causes optical path loss which limits overall system performance.

Figure 9:
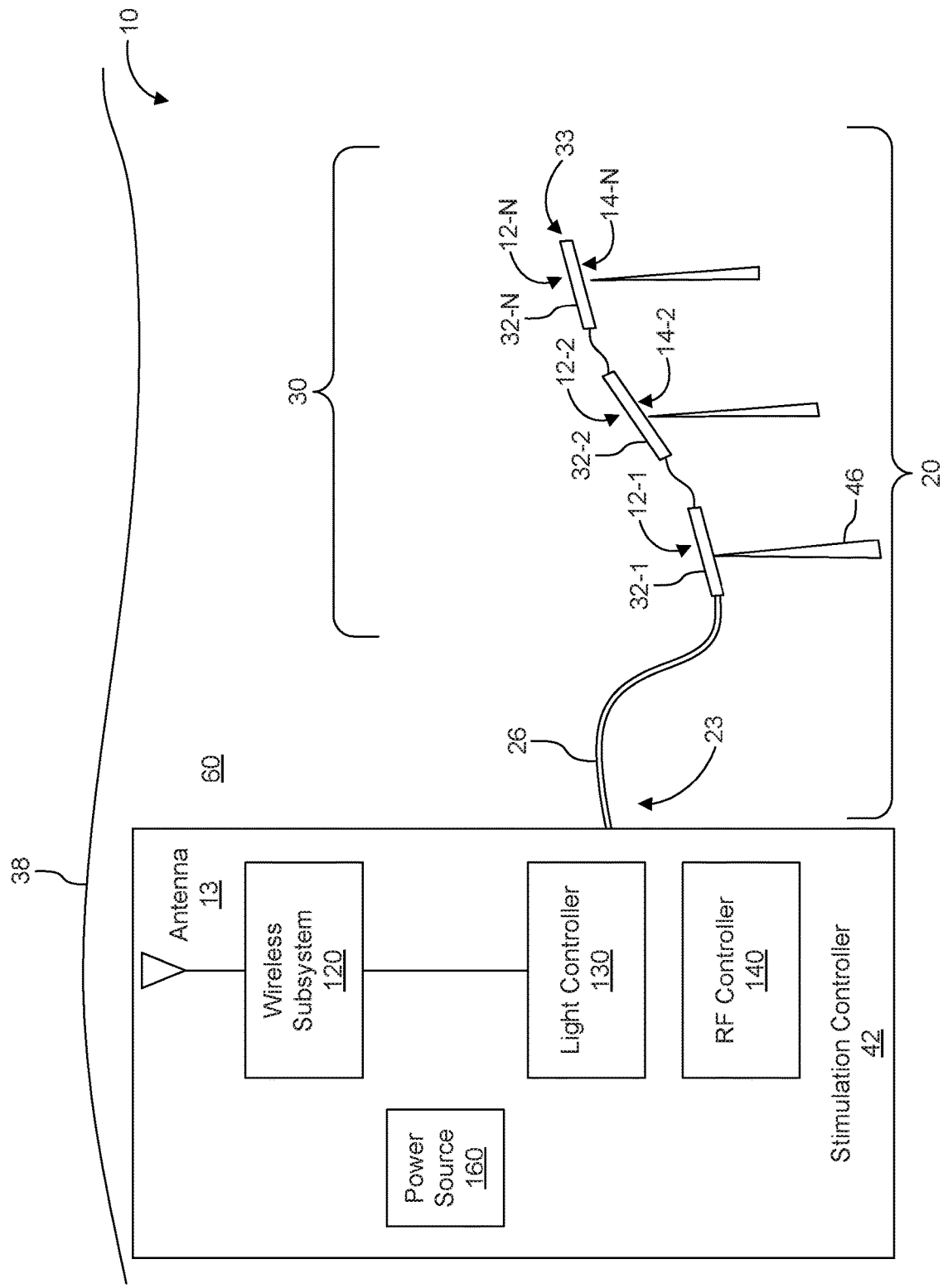
FIG. 9 is a schematic view showing a wireless embodiment of the stimulation controller to illustrate that the stimulation controller can also be implanted into the subject.

FIG. 9 shows an embodiment of the optical neurostimulation system 10 that can be entirely implanted within a subject 60. The stimulation controller 42 provides a wireless light generation capability via a wireless communications subsystem 120 and antenna 13. The stimulation controller 42 device has an internal power source 160 such as a battery or super capacitor. In one implementation, the power source 160 can be recharged inductively via an inductive power transmitter placed upon the power source at the skin boundary 38 of the implantation site of the stimulation controller 42.

As with the optical neurostimulation system 10 of FIG. 1, the system 10 of FIG. 9 includes the necessary electronics for the generation of RF signals 19 and optical signals 11 and includes the optical drive lines 17 and RF drive lines 15. An enclosure material of the stimulation controller 42 in this example is a biocompatible material suitable for temporary or permanent implantation, such as medical grade silicone, in one example.

The optical drive lines 17 that carry the optical signals 11 can also be replaced with light sources 27 that are local to the light emitter modules 32. In one example, small LEDs mounted at the light emitter modules 32 can supply the optical signals 11 to one or more of the light emitter modules 32.

Figure 10:
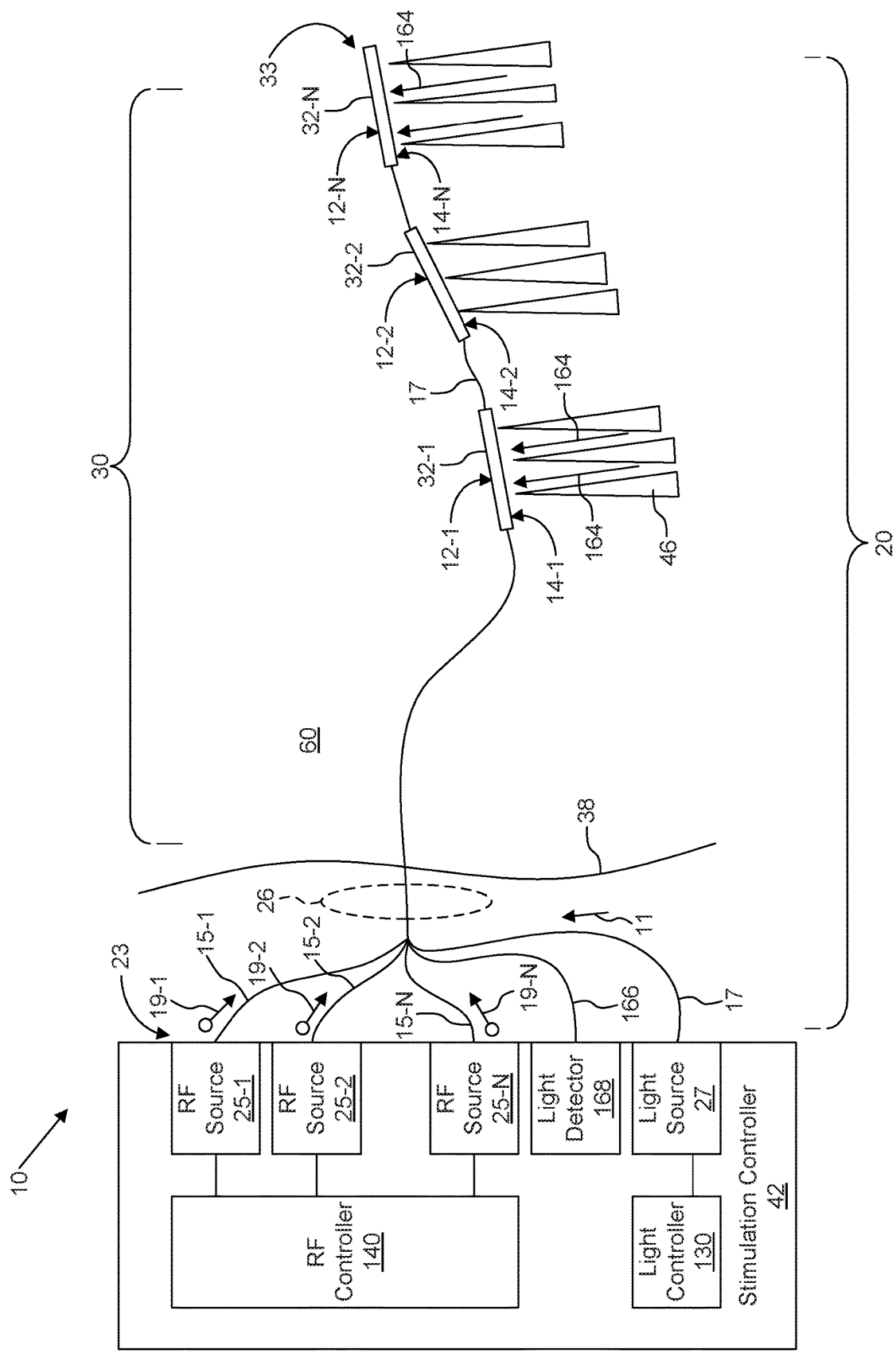
FIG. 10 is a schematic diagram of an optical neurostimulation and detection system that includes an implantable lead body of a medical lead device and a stimulation controller and detector, where the lead body includes light emitter/detector modules that couple light signals from a light source into modulated light signals that are emitted from the light emitter modules to stimulate neural tissue and/or neural cells of a subject and also collect light from the tissue for detection and analysis.

FIG. 10 is a schematic diagram of an exemplary optical neurostimulation and detection system 10, which has been constructed according to the principles of the present invention.

As described earlier, the system 10 also includes the stimulation controller 42 and the medical lead device 20. The medical lead device 20 has an elongated lead body 30 and a flexible umbilical tether 26. A distal end 33 of the medical lead device 20 includes one or more light emitter modules 32 of the lead body 30 and a proximal end 23 of the medical lead device 20 includes radio frequency (RF) and optical terminations of the flexible umbilical tether 26.

This embodiment also makes provisions for the detection of light from the tissue 99. This provides for a 'closed-loop implementation' enabling stimulation and detection. As before, the tissue is stimulating with light. Here, however, the light emitter modules 32 of the lead body 30 also function as detection modules that receive light 164 generated or transmitted from the tissue 99. This light might be light from voltage sensitive dyes (VSDs). In this instance, the cells would be illuminated by a fluoresce wavelength and the cells would fluoresce when action potentials are present across the membrane. In another case, action potentials are read by measuring small changes in birefringence.

Specifically, the light 164 from the tissue is collected by light emitter/detector modules 32 and converted into an electrical pulse sent locally to the modules with small detectors or transmitted back to the stimulation controller via the same optical drive lines 17 or a separate optical detection fiber 166 to be detected by a detector 168 of the controller 42.

While this invention has been particularly shown and described with references to preferred embodiments thereof, it will be understood by those skilled in the art that various changes in form and details may be made therein without departing from the scope of the invention encompassed by the appended claims.

What is claimed is:

1. An optical neurostimulation system, comprising:
   a medical lead device including an implantable lead body; and
   one or more light emitter modules of the lead body that generate modulated light signals for the irradiation of neural tissue of a subject, and
   wherein the lead body includes one or more radio frequency, (RF) drive lines that connect to and enable the one or more light emitter modules to receive RF signals which control the generation of the modulated light signals from light signals.

2. The system of claim 1, wherein the one or more light emitter modules are attached to a substrate of the lead body.

3. The system of claim 1, wherein the one or more light emitter modules are molded into a substrate of the lead body.

4. The system of claim 1, further comprising a nerve cuff for attaching the light emitter modules onto the neural tissue of the subject.

5. The system of claim 1, wherein the lead body includes one or more optical drive lines that connect to and enable the one or more light emitter modules to receive light signals.

6. An optical neurostimulation system, comprising: a medical lead device including an implantable lead body; and one or more light emitter modules of the lead body that generate modulated light signals for the irradiation of neural tissue of a subject, wherein the one or more light emitter modules include Surface Acoustic Wave (SAW) substrates in which SAWs are generated to couple the modulated light signals into the neural tissue.

7. The system of claim 6, wherein the lead body includes one or more radio frequency (RF) drive lines that connect to and enable the one or more light emitter modules to receive RF signals which control the generation of the SAWs.

8. The system of claim 6, wherein the modulated light signals are emitted from a distal face of the one or more light emitter modules.

9. The system of claim 1, further comprising a stimulation controller that includes a light source and a RF source that generates the RF signals to modulate light signals into the modulated light signals provided by the one or more light emitter modules.

10. The system of claim 9, wherein the stimulation controller is implantable.

11. The system of claim 1, wherein the one or more light emitter modules are arranged around the lead body in circumferential fashion.

12. The system of claim 1, wherein the one or more light emitter modules comprises a two dimensional array of display elements.

13. The system of claim 12, wherein the two dimensional array of display elements are wrapped into a tubular configuration.

14. The system of claim 12, further comprising light directing elements arranged over the two dimensional array of display elements.

15. The system of claim 14, wherein the light directing elements are lenslets or directional gratings.

16. A medical lead device, comprising:
an implantable lead body;
a flexible umbilical tether including optical drive lines that provide light signals to the lead body; and
one or more light emitter modules of the lead body that generate modulated light signals from the light signals, the modulated light signals being emitted through from the one or more light emitter modules to stimulate neural cells and/or neural tissue of a subject, and
wherein the umbilical tether includes one or more radio frequency (RF) drive lines that connect to and enable the one or more light emitter modules to receive RF signals which control the generation of the modulated light signals from the light signals.

17. The device of claim 16, further comprising a nerve cuff for attaching the light emitter modules onto the neural tissue of the subject.

18. A medical lead device, comprising: an implantable lead body; a flexible umbilical tether including optical drive lines that provide light signals to the lead body; one or more light emitter modules of the lead body that generate modulated light signals from the light signals, the modulated light signals being emitted from the one or more light emitter modules to stimulate neural cells and/or neural tissue of a subject; and a nerve cuff for attaching the light emitter modules onto the neural tissue of the subject, wherein the one or more light emitter modules include Surface Acoustic Wave (SAW) substrates in which SAWs are generated to couple the modulated light signals into the neural tissue.

19. The device of claim 18, wherein the umbilical tether includes one or more radio frequency (RF) chive lines that connect to and enable the one or more light emitter modules to receive RF signals which control the generation of the SAWs.

20. The device of claim 19, wherein the modulated light signals are emitted from a distal face of the one or more light emitter modules.

21. A medical lead device, comprising:

an implantable lead body;

a flexible umbilical tether including optical drive lines that provide light signals to the lead body and one or more radio frequency (RF) drive lines for providing RF signals; and one or more light emitter and detector modules that provide light to stimulate neural cells and/or neural tissue of a subject and that collect light from the tissue or cells, one or more RF generators that provide the RF signals to control the generation provision of the light to stimulate the neural cells and/or the neural tissues and to collect the light from the tissue or cells.

* * * * *